United States Patent [19]

Gatzen et al.

[11] 4,272,548

[45] Jun. 9, 1981

[54] PROCESS FOR THE LOWERING OF INCREASED LEVELS OF CHOLESTEROL AND NEUTRAL FAT IN THE BLOOD OF HUMANS

[76] Inventors: Carl-Jacob Gatzen, Pannebäckerstr. 20; Hartmut Poethen, Berger Allee 3; Heribert Sion, Graf-Adolf-Platz 3, all of Düsseldorf, Fed. Rep. of Germany

[21] Appl. No.: 121,688

[22] Filed: Feb. 15, 1980

[30] Foreign Application Priority Data

Feb. 16, 1979 [DE] Fed. Rep. of Germany ........ 2905979

[51] Int. Cl.$^3$ .............................................. A61K 31/23
[52] U.S. Cl. ..................................................... 424/312
[58] Field of Search ......................................... 424/312

[56] References Cited

U.S. PATENT DOCUMENTS

| | | | |
|---|---|---|---|
| 3,158,541 | 11/1964 | Sutherland | 424/312 |
| 3,192,057 | 6/1965 | Hines et al. | 426/532 |
| 3,203,862 | 8/1965 | Jones | 424/312 |
| 3,388,085 | 6/1968 | Levkoff et al. | 426/92 |
| 3,495,011 | 2/1970 | Fossel | 424/312 |
| 4,034,083 | 7/1977 | Mattson | 424/312 X |

FOREIGN PATENT DOCUMENTS

1767439  5/1968  Fed. Rep. of Germany .
2030429  6/1970  Fed. Rep. of Germany .

OTHER PUBLICATIONS

Die Fleischwirtschaft, Apr. 1971, pp. 517–522; Dec. 1968, pp. 1594–1596; Jul. 1972, pp. 816–818.
Chem. Abstr. 88:21033v, 1978.

*Primary Examiner*—Frank Cacciapaglia, Jr.
*Attorney, Agent, or Firm*—Dennis P. Clarke

[57] ABSTRACT

The present invention is related to a process for the lowering of increased cholesterol and/or increased neutral fat levels in the blood of humans by administering to such humans a completely acetylated monoglyceride having the general formula

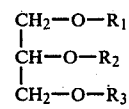

wherein one of the groups $R_1$, $R_2$ and $R_3$ is the acyl radical of a fatty acid having from 12 to 22 carbon atoms while the other two groups represent acetyl groups, or a mixture of several such completely acetylated monoglycerides, preferably orally and in a daily dosage ranging from 1 to 15 cc. of the pure acetylated monoglyceride or mixture of such acetylated monoglycerides, either in pure form or together with usual pharmaceutical carriers or diluents, possibly together with other lipid lowering agents, or incorporated in dietetic food products.

3 Claims, No Drawings

PROCESS FOR THE LOWERING OF INCREASED LEVELS OF CHOLESTEROL AND NEUTRAL FAT IN THE BLOOD OF HUMANS

The present invention is related to a process for the lowering of too high cholesterol levels and/or too high neutral fat levels in the blood of human beings. The invention is further related to a process for supporting the treatment of such deficiency by means of pharmaceutical preparations usually used therefor.

An increased cholesterol level in the blood of humans is caused by defects in the fat metabolism. According to the present knowledge of the experts in this field, such increased cholesterol levels are the reason for arteriosclerosis and hypertonia which again may cause an increased susceptibility to myocardial infarction and other serious circulatory disorders or diabetes or disorders in the functioning of the thyroid gland. Furthermore, increased fat levels in the blood which often but not always accompany increased cholesterol levels, also may cause serious disorders.

There are known many pharmaceutical products for the lowering of increased cholesterol and/or neutral fat levels in human blood such as lipid lowering products containing in particular 2-(4-chlorophenoxy)-2-methyl-propionic acid ethyl ester (generic name: clofibrate) as active agent for lowering the cholesterol level. As is known from publications, clofibrate has serious disadvantages (see for instance British Heart Journal 1978, vol. 40, p. 1069–1118). In addition thereto, it may be often observed that such products only yield into an insufficient lowering of high cholesterol levels often up to 500 mg. per 100 ml. or produce resistancy in other respects after a certain period of treatment, and this despite a contemporary low fat diet. In patients suffering from contemporary increased neutral fat blood levels, combination products have to be used containing nicotinic acid derivatives such as beta-pyridyl carbinol hydrogentartrate or inositol nicotinate as active agent.

It is an object of the present invention to provide an improved process for the treatment of humans suffering from increased cholesterol and/or neutral fat levels in their blood. It is a further object of the present invention to provide a process by which the treatment of humans suffering from such deficiency by usual pharmaceutical products therefor is supported in particular in patients showing resistancy in the therapy with such pharmaceutical products.

It has been found that increased cholesterol levels in the blood of humans and contemporary increased neutral fat levels or only increased neutral fat levels may be rapidly lowered to normal levels without any undesired side effects by administering to such humans a completely acetylated monoglyceride of general formula

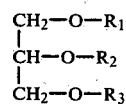

wherein one of the groups $R_1$, $R_2$ and $R_3$ is the acyl radical of a saturated or olefinically unsaturated fatty acid having from 12 to 22 carbon atoms while the other two groups represent acetyl groups, or a mixture of several such completely acetylated monoglycerides. It has been furthermore found that therapy resistancy against usual pharmaceutical preparations for the treatment of such deficiency may effectively be overcome by administering to such patients one or a mixture of several of such completely acetylated monoglycerides, and this even if the patient suffering from such increased cholesterol levels does not follow a low fat diet at all or not continuously.

The acetylated monoglycerides used in the process according to the present invention are used as such as pharmaceutical preparation, i.e. in pure form, or in admixture with usual carrier materials or diluent or are used in admixture to dietetic products. They are preferably administered orally. They are used in dosages ranging from 1 to 15 cc. calculated to the pure form, per administration and may be administered several times a day at appropriate intervals. The upper limit is of less importance in view of the very low toxicity of such acetylated monoglycerides. The dosage, the intervals of administration and the duration of the treatment depend upon the degree of the increased cholesterol and/or neutral fat blood level and the response of the patient treated therewith in the cholesterol and/or neutral blood level. Treatment may be carried on for months without undesired side effects until a normal blood level has been stabilized.

The acetylated monoglycerides used according to the present invention may furthermore be used together with the vitamins and/or phospholipids as they are used in lipid lowering products or they may be combined with other additives used for this purpose such as desoxycholic acid. In particular a combination with vitamin A, D and/or E and/or the phospholipids may be useful because these products are soluble in the acetylated monoglycerides.

The active agents used in the present process represent known products which up to now have been used as coating materials for foodstuffs such as meat products in order to avoid mould growth during storage (see for instance U.S. Pat. No. 3,192,057, U.S. Pat. No. 3,388,085, German Offenlegungsschrift No. 17 67 439 and "Die Fleischwirtschaft", 1968, p. 1594 to 1596; 1971, p. 517 to 522; and 1972, p. 816 to 818). The active agents used in the present process represent a completely acetylated monoglyceride, preferably prepared from lard, cottonseed oil or partially hydrogenated vegetable oil and distilled after production, or represent a mixture of several such acetylated monoglycerides. Thus, the active agent represent an acetylated monoglyceride wherein the number of carbon atoms in the acyl group and the percentage of unsaturated acyl groups over saturated groups corresponds to that in the lard, the cottonseed oil or, respectively, the partially hydrogenated vegetable oil started from. The most often occuring fatty acid radicals are those of stearic, palmitic and oleic acid. The present invention therefore also comprises the use of a substantially corresponding mixture of the various singular synthetically produced diacetyl monoglycerides. It is however preferred to use acetylated monoglycerides produced from such neutral fats. Most preferred are such acetylated monoglycerides which are produced from lard. Such products are commercially available, for instance under the brand name MYVACET from the Distillation Products Industries Division of Eastman Kodak Co., Rochester, N.Y. or under the brand names DERMATEX and SKINTEX from H. Stemmler, Cologne, Federal Republic or Germany.

The production of the acetylated monoglycerides used in the process of the present invention occurs in manners known per se by reesterification in the presence of catalysts and a subsequent molecular distillation. The monoglycerides also can be prepared in manners known per se by direct acetylation of the monoglycerides with acetic acid anhydride without catalysts and without molecular distillation, the possibly formed acetic acid, acetic acid anhydride and glycerol triacetate being removed by high vacuum distillation.

The distilled, completely acetylated monoglyceride preferably produced from lard (hereinafter refer to as monoglyceride SCH) represents a clear, almost colorless liquid having a solidification point of about +8° C., a refractory index of 1447 at 40° C. and of 1443 at 50° C., a viscosity of 50 cP at +20° C. and of 19 cP at +50° C., a specific gravity of 0.99 at +20° C. and of 0.96 at +50° C., an iodine number of 42, a saponification number of 380, a monoglyceride content of from 0 to 2%, a Reichert-Meissel-number of 145, an acid number of less than 4, and a peroxide number of less than 2.

The distilled, completely acetylated monoglyceride produced from a partially hydrated vegetable oil (hereinafter referred to as monoglyceride PF) represents a clear and almost colorless liquid, having a solidification point at about +7° C., a refractory index of 1447 at 40° C., a viscosity of 56 cP at +20° C. and of 19 cP at +50° C., a gravity of 0.98 at +20° C. and of 0.96 at +50° C., an iodine number of 44, a saponification number of 380, a monoglyceride content of from 0 to 2%, a Reichert-Meissel-number of 146, and an acid number of less than 4.

The distilled, fully acetylated monoglyceride produced from cottonseed oil (hereinafter refer to as monoglyceride BW) represents a clear, slightly yellow colored liquid having a solidification point of about +1° C., a refractory index of 1451 at 40° C., a viscosity of 47 cP at +20° C. and of 18 cP at +50° C., a gravity of 0.98 at +20° C. and of 0.96 at +50° C., an iodine number of 70, a saponification number of 380, a monoglyceride content of from 0 to 2%, a Reichert-Meissel-number of 145, and an acid number of less than 4.

EXAMPLES

1. A female patient of 50 years of age suffering from a hyperlipidemia 2b had a cholestrol blood level of 354 mg. per 100 ml. and a neutral fat blood level of 122 mg. per 100 ml. at the beginning of the treatment (June 1). The patient received for 10 days 1 teaspoon of the monoglyceride SCH three times a day, and thereafter a daily dose of three times half a teaspoon. After 37 days (July 7) the cholesterol blood level was at 307 mg. per 100 ml. and the neutral fat level was at 107 mg. per 100 ml. and after two further months of treatment (September 8) a 231 and 136 mg. per 100 ml., respectively, and after another month of treatment (October 5) at a daily dose of three times half a teaspoon the blood levels were at 254 and 107 mg. per 100 ml., respectively. The dose was increased to the initial dose. After about another month of treatment (November 2) and three months thereafter (January 11) the cholesterol and neutral fat level was 233 and 106 mg. per 100 ml., respectively, and after further three months of treatment the levels were at 200 and 104 mg. per 100 ml., respectively. The treatment was finished at December 15. Despite unrestricted food consumption during the Christmas holiday season the blood levels remained in the physiologically normal area. Thus, in addition to a lowering of the blood levels, the treatment also produced a stabilizing effect on the cholesterol and neutral fat blood levels. 2. A patient 73 years of age and suffering from diabetes mellitus, sclerosis of the aortas, heart insufficiency and hyperlipidemia 2b showed a cholesterol level of 426.6 mg. per 100 ml. and a neutral fat blood level of 169 mg. per 100 ml. at the beginning of the therapy (January 13). In addition to a diet, the patient received 750 mg. of clofibrate per day. After about three months (April 21) the cholesterol blood level was at 418 mg. per 100 ml. and a neutral fat blood level was at 211 mg. per 100 ml. In addition to a diet, the treatment was continued with the administration of three times per day of a capsule containing 500 mg. of clofibrate and 300 mg. of inositol nicotinate. After one month (May 26) the cholesterol and neutral fat blood levels were at 318 and 149 mg. per 100 ml., respectively. The treatment with the combination product had to be stopped because of generalized pruritus. The patient was further treated with the monoglyceride SCH at a dosage of three times one teaspoon per day for 10 days and thereafter at a dosage of three times half a teaspoon per day. The blood fat content decreased considerably. After one month (June 30) the cholesterol and neutral fat blood level was at 212 and 107 mg. per 100 ml., respectively. There was no indication of incompatibility or other undesired side effect.

What we claim is:

1. A process for lowering increased cholesterol and neutral fat levels in the blood of humans comprising orally administering to said humans a cholesterol and neutral fat level reducing amount of a completely acetylated monoglyceride having the formula:

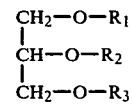

wherein one of the groups $R_1, R_2$ and $R_3$ is the acyl radical of a saturated or olefinically unsaturated fatty acid having from 12 to 22 carbon atoms and the other two groups represent acetyl groups, or a mixture of several such completely acetylated monoglycerides.

2. The process of claim 1 wherein said monoglyceride or mixture of monoglycerides is administered admixed with a dietetic food product.

3. The process of claim 1 wherein said monoglyceride or mixture of monoglycerides is administered before, after or contemporaneously with known compounds for lowering increased cholesterol and neutral fat levels in the blood of humans.

* * * * *